United States Patent
Hanieh

(10) Patent No.: US 11,654,138 B2
(45) Date of Patent: *May 23, 2023

(54) THERAPEUTIC AGENTS FOR TREATING AND PREVENTING AUTOIMMUNE DISEASES AND CANCER AND A SCREENING METHOD

(71) Applicant: KING FAISAL UNIVERSITY, Hofouf (SA)

(72) Inventor: Hamza Naim Ahmad Hanieh, Aqaba (JO)

(73) Assignee: KING FAISAL UNIVERSITY, Hofouf (SA)

(*) Notice: Subject to any disclaimer, the term of this patent is extended or adjusted under 35 U.S.C. 154(b) by 307 days.

This patent is subject to a terminal disclaimer.

(21) Appl. No.: 17/191,562

(22) Filed: Mar. 3, 2021

(65) Prior Publication Data

US 2021/0186944 A1    Jun. 24, 2021

Related U.S. Application Data

(60) Division of application No. 16/920,584, filed on Jul. 3, 2020, now abandoned, which is a continuation-in-part of application No. 16/717,727, filed on Dec. 17, 2019, now Pat. No. 10,709,696, which is a continuation of application No. 16/396,719, filed on Apr. 28, 2019, now Pat. No. 10,512,639.

(51) Int. Cl.
*A61K 31/4439* (2006.01)
*G01N 33/50* (2006.01)

(52) U.S. Cl.
CPC ....... *A61K 31/4439* (2013.01); *G01N 33/502* (2013.01)

(58) Field of Classification Search
CPC .......................... A61K 31/4439; G01N 33/502
See application file for complete search history.

(56) References Cited

U.S. PATENT DOCUMENTS

| 10,512,639 B1* | 12/2019 | Hanieh | ............... G01N 33/502 |
| 10,717,727 B2* | 7/2020 | Dutt | ..................... C07C 53/126 |
| 2018/0016576 A1 | 1/2018 | Kishimoto et al. | |
| 2018/0195064 A1 | 6/2018 | Kishimoto et al. | |

FOREIGN PATENT DOCUMENTS

JP    6069075 A    4/1985

OTHER PUBLICATIONS

Kumar, B., et al., "Latest Update on Pharmacological Activities of 1,3,4-Oxadiazole Derivatives," J. Cell Sci. Ther., 7:1, (2016).
Hanieh, H., et al., "Arid5a Stabilizes OX40 mRNA in murine CD4+ T cells by recognizing a stem-loop structure in its 3'UTR," Eur. J. Immunol., 48(4): pp. 593-604, (2018).
Masuda, K., "Arid5a regulates naive CD4+ T cell fate through selective stabilization of Stat3 mRNA," JEM, 213(4): pp. 605-619 (2016).
Masuda, K., "Arid5a controls IL-6 mRNA stability, which contributes to elevation of IL-6 level in vivo," PNAS, 110(23) pp. 9409-9414 (2013).
Zaman, M. M. et al., "Arid5a exacerbates IFN-y-mediated septic shock by stabilizing T-bet mRNA," PNAS, 113(41) pp. 11543-11548 (2016). Any identified foreign patents and/or publications were properly submitted in parent application U.S. Appl. No. 16/920,584, filed Jul. 3, 2021, the priority of which is claimed.

* cited by examiner

*Primary Examiner* — Svetlana M Ivanova
(74) *Attorney, Agent, or Firm* — Nath, Goldberg & Meyer; Richard C. Litman

(57) ABSTRACT

A method for treating and preventing autoimmune diseases and cancer can include administering to a subject in need thereof a therapeutically effective amount of a pharmaceutical composition comprising an Arid5a inhibitor and a pharmaceutically acceptable carrier. A screening method can include identifying candidate Arid5a inhibitors through in silico predicted binding to Arid5a target domains (Pocket X) and confirming Arid5a inhibition through in vitro by binding and luciferase assays.

4 Claims, 11 Drawing Sheets

Specification includes a Sequence Listing.

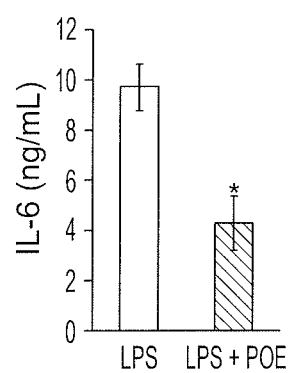 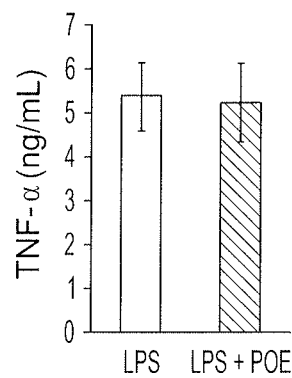
*FIG. 3A*     *FIG. 3B*
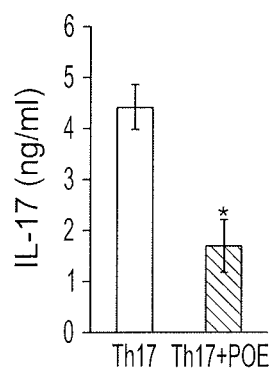 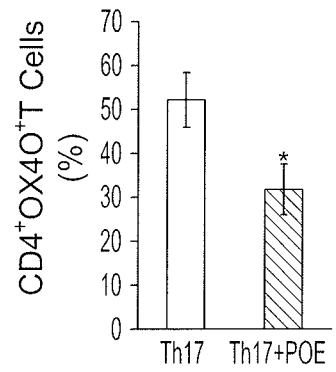 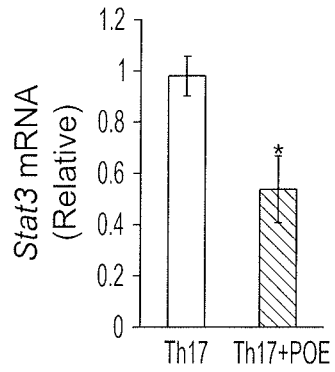
*FIG. 3C*     *FIG. 3D*     *FIG. 3E*

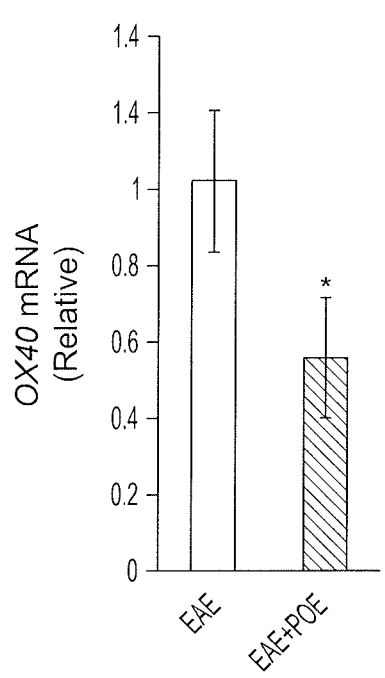 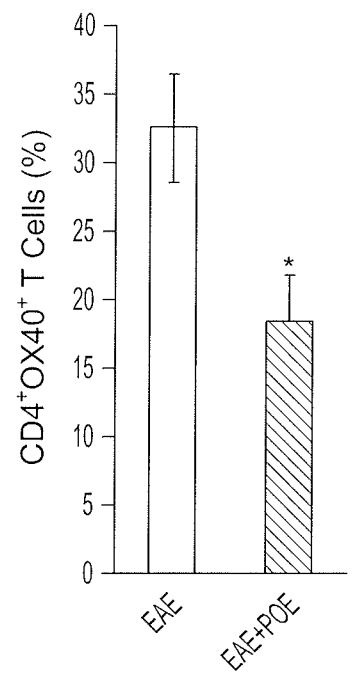
FIG. 5D  FIG. 5E

SEQUENCE LISTING

```
<160> NUMBER OF SEQ ID NOS: 2

<210> SEQ ID NO 1
<211> LENGTH: 100
<212> TYPE: PRT
<213> ORGANISM: Mus musculus

<400> SEQUENCE: 1

Gln Glu Glu Glu Gln Ala Phe Leu Val Ser Leu Tyr Lys Phe Met Lys
1               5                   10                  15

Glu Arg His Thr Pro Ile Glu Arg Val Pro His Leu Gly Phe Lys Gln
                20                  25                  30

Ile Asn Leu Trp Lys Ile Tyr Lys Ala Val Glu Lys Leu Gly Ala Tyr
            35                  40                  45

Glu Leu Val Thr Gly Arg Arg Leu Trp Lys Asn Val Tyr Asp Glu Leu
        50                  55                  60

Gly Gly Ser Pro Gly Ser Thr Ser Ala Ala Thr Cys Thr Arg Arg His
65                  70                  75                  80

Tyr Glu Arg Leu Val Leu Pro Tyr Val Arg His Leu Lys Gly Glu Asp
                85                  90                  95

Asp Lys Pro Leu
            100

<210> SEQ ID NO 2
<211> LENGTH: 22
<212> TYPE: RNA
<213> ORGANISM: Mus musculus

<400> SEQUENCE: 2
uccacaccgu ucuaggugcu gg                                          22
```

THERAPEUTIC AGENTS FOR TREATING AND PREVENTING AUTOIMMUNE DISEASES AND CANCER AND A SCREENING METHOD

CROSS-REFERENCE TO RELATED APPLICATION

This application is a division of U.S. patent application Ser. No. 16/920,584, filed Jul. 3, 2020, pending, which is a continuation-in-part of U.S. patent application Ser. No. 16/717,727, filed on Dec. 17, 2019, now U.S. Pat. No. 10,709,696, issued Jul. 14, 2020, which is a continuation of U.S. patent application Ser. No. 16/396,719, filed on Apr. 28, 2019, now U.S. Pat. No. 10,512,639, issued Dec. 24, 2019.

INCORPORATION BY REFERENCE OF MATERIAL SUBMITTED IN COMPUTER READABLE FORM

The Applicants hereby incorporate by reference the sequence listing contained in the ASCII text file titled 32087_15_sequence_listing_ST25.txt, created Dec. 5, 2018 and having 1.23 KB of data.

BACKGROUND

1. Field

The disclosure of the present patent application relates to RNA-binding protein (RBP) inhibitors, and particularly, to Arid5a inhibitors, methods of screening for Arid5a inhibitors, and methods of treating autoimmune diseases and cancer using an Arid5a inhibitor.

2. Description of the Related Art

Inflammation, a body response to an injury, is divided into acute and chronic inflammation, wherein the chronic inflammation is a long-lasting event usually over months and years. Autoimmune diseases are chronic inflammatory diseases caused when a subject's own immune system attacks otherwise healthy cells in the body. Common autoimmune diseases include multiple sclerosis (MS), rheumatoid arthritis (RA), psoriasis, inflammatory bowel disease (IBD), lupus, type 1 diabetes, Graves' disease, and Guillan-Barre syndrome. Common symptoms of autoimmune diseases include fatigue, joint pain and swelling, skin problems, abdominal pain or digestive issues, recurring fever, swollen glands, and metabolic issues. Current treatments for autoimmune diseases are focused on alleviating symptoms and include primarily non-steroidal anti-inflammatory drugs (NSAIDs) and drugs intended to suppress the immune response. The NSAIDS treatments, as immune suppressants, are both limited in their impact and have significant harmful side effects.

Regardless of the site of inflammation associated with the autoimmune disease (for example, neuron in MS, joints in RA and the skin in psoriasis), they all share several pathophysiological features. The primary drivers of these features are pro-inflammatory cytokines and mediators. MS, as a representative of autoimmune diseases, involves both the innate and adaptive immune responses.

Innate immune cells, such as macrophages, contribute to pathogenesis of MS by secretion of pro-inflammatory cytokines such as interleukin-6 (IL-6) and tumor necrosis factor-α (TNF-α). In addition, the antigen-presenting cells (APCs) of the innate immune response provide cytokine milieus that direct differentiation of naïve CD4$^+$ T cells into effector cells. These differentiated cells, mainly IL-17-secreting T helper 17 (Th17) cells are implicated in MS pathogenesis. Therefore, reducing any or all of the above mentioned pro-inflammatory cytokines, which are greatly implicated in autoimmune inflammation, has been an area of active investigation to develop a therapeutic strategy to treat MS.

Common treatments for MS and other autoimmune diseases typically focus on reducing exacerbations and disease progression rather than offering a cure. These treatments are classified as disease-modifying treatments (DMT). For example, interferon-β (IFN-β) has been used as an efficient DMT in MS patients. However, this treatment is associated with increased levels of liver enzymes and flu-like symptoms. Other therapeutic agents such as mitoxantrone and humanized antibodies including daclizumab, natalizumab and alemtuzumab exert promising therapeutic effects in MS patients. However, recent studies have shown that such treatments have severe side effects. Mitoxantrone is associated with cardiotoxicity and acute leukemia, alemtuzumab is associated with autoimmune-associated complications, and natalizumab is associated with progressive multifocal leukoencephalopathy.

Cancer is a disease caused by dysregulation of the cell division cycle, resulting in an uncontrolled growth of cells. Cancers are categorized based upon the cell type from which the cancer originated. Common cancers include breast cancer, prostate cancer, basal cell cancer, melanoma, colon cancer, lung cancer, leukemia, and lymphoma. Generally, cancer treatments focus on killing rapidly dividing cells. Common treatments include radiation therapies and chemotherapies. More recent treatments have been able to target some specific types of cancer cells. However, most cancer treatments have significant side effects and are not always well tolerated.

Thus, alternative therapeutic agents for treating and preventing autoimmune diseases and cancer and screening methods for agents solving the aforementioned problems are desired.

SUMMARY

Therapeutic agents for treating and preventing autoimmune diseases and cancer can include compositions comprising an AT-rich interactive domain containing 5a (Arid5a) inhibitor. The autoimmune diseases can include diseases associated with chronic inflammation. The autoimmune diseases can include but are not limited to, multiple sclerosis, rheumatoid arthritis, and psoriasis. The cancer may include but is not limited to, breast cancer, prostate cancer, and lung cancer. The Arid5a inhibitor can inhibit the RNA-binding activities of Arid5a and the subsequent stabilizing functions on target mRNAs encoding pro-inflammatory mediators. The Arid5a inhibitor can include 1-Phenyl-2-(5-pyridin-4-yl-[1,3,4]oxadiazol-2-ylsulfanyl)-ethanone (herein, "POE"), having a chemical structure according to the formula:

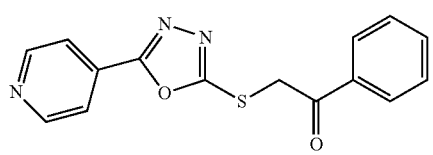 [SMILES: O=C(CSc1nnc(-c2ccncc2)o1)c1ccccc1]

or a pharmaceutically acceptable salt thereof. It should be understood that the Arid5a inhibitor POE includes analogs of POE having any dihedral angles.

In an embodiment, the Arid5a inhibitors may include POE analogs having a chemical structure according to the following general formula:

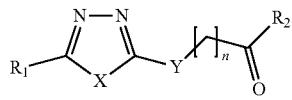

wherein each of $R_1$ and $R_2$ is independently selected from H, alkyl, phenyl, substituted phenyl, a 5-membered heteroaryl, and 6-membered heteroaryl; each of X and Y is independently selected from S, O, and NH; and n is an integer representing a number of Cs selected from 0, 1, and 2. Preferably, n is 1.

In an embodiment, the POE analogs include but are not limited to:

POE A1

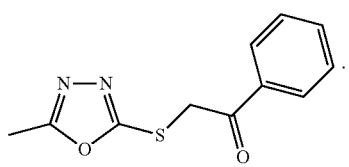

In an embodiment, the POE analog is

POE A2

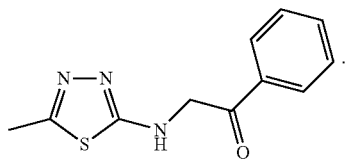

In an embodiment, the POE analog is

POE A3

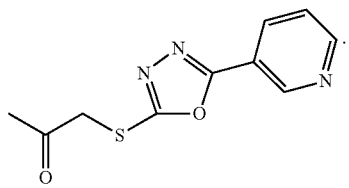

It should be understood that POE analogs POE A1, POE A2 and POE A3 are shown for illustrations purposes only, and the Arid5a inhibitors include POE analogs having the chemical structure according to the general formula.

In a further embodiment, a method for treating and preventing autoimmune diseases and cancer can include administering to a subject in need thereof a therapeutically effective amount of a pharmaceutical composition comprising one or more (Arid5a) inhibitors alone or combined with other therapeutic or prophylactic agents.

These and other features of the present disclosure will become readily apparent upon further review of the following specification and drawings.

BRIEF DESCRIPTION OF THE DRAWINGS

FIG. 3A depicts a graph of the effects of POE on IL-6 production by macrophages.

FIG. 3B depicts a graph of the effects of POE on TNF-α production by macrophages.

FIG. 3C depicts a graph of the effects of POE on IL-17 production by differentiated Th17 cells.

FIG. 3D depicts a graph of the effects of POE on CD4$^+$ OX40$^+$ T cells in differentiated Th17 cells.

FIG. 3E depicts a graph of the effect of POE on Stat3 mRNA expression in differentiated Th17 cells.

FIG. 5D depicts a graph of OX40 mRNA levels in CD4$^+$ T cells isolated from the CNS in the EAE model with and without treatment with POE.

FIG. 5E depicts a graph of percentage of CD4$^+$OX40$^+$ T cells isolated from the CNS in EAE model with and without treatment with POE.

FIG. 6 depicts a graph of the efficient inhibitory effects of POE and its example analogs POE A1-A3 on Arid5a stabilizing function on Il6 3'UTR through the target domain of Arid5a.

Similar reference characters denote corresponding features consistently throughout the attached drawings.

DETAILED DESCRIPTION OF THE PREFERRED EMBODIMENTS

Figure 1A:
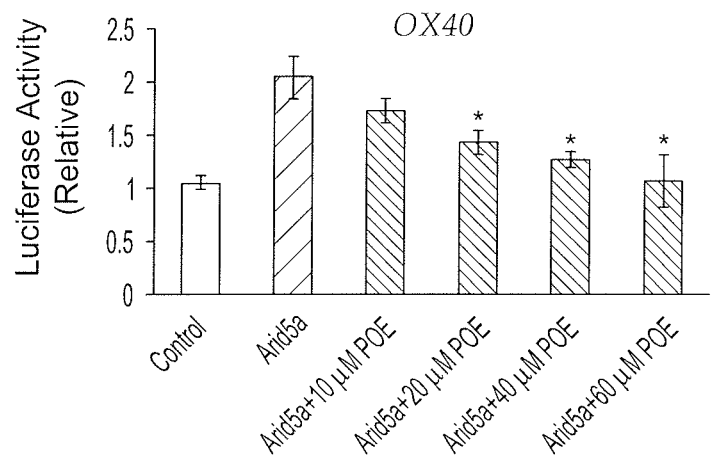
FIG. 1A depicts a graph of the effects of POE on Arid5a-mediated stability of the OX40 3'UTR.

As used herein, a "subject" includes mammals, e.g., humans, dogs, cats, sheep, cows, rats, mice, and the like.

As used herein, "Arid5a" refers to AT-rich interactive domain-containing 5a (Arid5A), a protein that stabilizes mRNAs encoding pro-inflammatory mediators, including signal transducer and activator of transcription 3 (Stat3), Il6, and OX40 (CD134).

As used herein, "effective amount" refers to an amount which provides a therapeutic or prophylactic benefit.

According to an embodiment, therapeutic agents for treating and preventing autoimmune diseases and cancer can include compositions comprising an AT-rich interactive domain containing 5a (Arid5a) inhibitor. The autoimmune diseases can include diseases associated with chronic inflammation. The autoimmune diseases can include but are not limited to, multiple sclerosis, rheumatoid arthritis, and psoriasis. The cancer may include but is not limited to, breast cancer, prostate cancer, and lung cancer. The Arid5a inhibitor can inhibit the RNA-binding activities of Arid5a and the subsequent stabilizing functions on target mRNAs encoding pro-inflammatory mediators. The Arid5a inhibitor can include 1-Phenyl-2-(5-pyridin-4-yl-[1,3,4]oxadiazol-2-ylsulfanyl)-ethanone (herein, "POE"), having a chemical structure according to the formula:

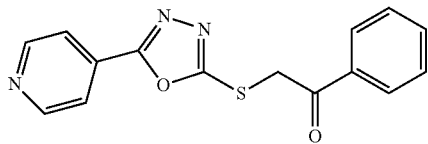 [SMILES: O=C(CSc1nnc(-c2ccncc2)o1)c1ccccc1]

or a pharmaceutically acceptable salt thereof. It should be understood that the Arid5a inhibitor POE includes analogs of POE having any dihedral angles.

In an embodiment, the Arid5a inhibitors include POE analogs having a chemical structure according to the following general formula:

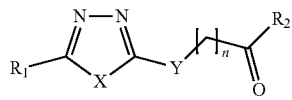

wherein each of $R_1$ and $R_2$ is independently selected from H, alkyl, phenyl, substituted phenyl, a 5-membered heteroaryl, and 6-membered heteroaryl; each of X and Y is independently selected from S, O, and NH; and n is an integer representing a number of Cs selected from 0, 1, and 2. Preferably, n is 1.

In a further embodiment, a method for treating and preventing autoimmune diseases and cancer can include administering to a subject in need thereof a therapeutically effective amount of a pharmaceutical composition comprising one or more (Arid5a) inhibitors alone or combined with other therapeutic or prophylactic agents.

Arid5a is required for pathogenesis of experimental autoimmune encephalomyelitis (EAE), a murine model of MS, by stabilizing the mRNAs of Il6 and OX40. Arid5a is also required for autoimmunity through promoting differentiation and effector functions of Th17 cells by stabilizing Stat3 and OX40 mRNAs. Accordingly, the Arid5a inhibitor can be administered to a subject to treat autoimmune diseases, including but not limited to MS, RA, and Psoriasis.

In a further embodiment, the Arid5a inhibitor can be used to prevent the proliferation of cancer cells. Arid5a inhibitors are herein shown to inhibit proliferation of a broad spectrum of cancer cells including breast cancer cells, lung cancer cells, and prostate cancer cells. Accordingly, in an embodiment the Arid5a inhibitor may be administered to a subject in need thereof to prevent the proliferation of cancer cells. In a further embodiment, the cancer cells, including but not limited to breast cancer cells, lung cancer cells, or prostate cancer cells.

An embodiment of the present subject matter is directed to a pharmaceutical composition comprising the Arid5a inhibitor compound and a pharmaceutically acceptable carrier. In an embodiment, the pharmaceutical composition includes the Arid5a inhibitor compound in combination with at least one of a therapeutic agent and a prophylactic agent.

An embodiment of the present subject matter is directed to a method of making the pharmaceutical composition including mixing the Arid5a inhibitor with a pharmaceutically acceptable carrier. For example, the method of making the pharmaceutical composition can include mixing the Arid5a inhibitor under sterile conditions with a pharmaceutically acceptable carrier and preservatives, buffers, or propellants to create the pharmaceutical composition; and presenting the pharmaceutical composition in a form suitable for daily, weekly, monthly, or life-long administration.

An embodiment of the present subject matter is directed to an analog or derivative of the Arid5a inhibitors described herein. In one embodiment, the Arid5a inhibitors described herein are candidates for derivatization. Thus, analogs of the Arid5a inhibitors described herein that have modulated potency, selectivity, and solubility are included herein and provide useful leads for drug discovery and drug development. In certain instances, during optimization new analogs are designed considering issues of drug delivery, metabolism, novelty, and safety.

In an embodiment, the composition of the present subject matter may be administered orally, nasally, rectally, parenterally, intracisternally, intra vaginally, intraperitoneally, topically, transdermally, by surgical implantation, or by intravenous or intramuscular injections. In an embodiment, the composition of the present subject matter is administered in a form selected from liquid oral preparations, solid oral preparations, parenteral preparations, injectable suspensions, and liposomes.

The Arid5a inhibitors or pharmaceutical compositions can be administered to a subject by any suitable route. For example, the compositions can be administered orally (including bucally and sublingually), nasally, rectally, intracisternally, intra vaginally, intraperitoneally, topically, transdermally (as by powders, ointments, or drops), parenterally, and/or by surgical implantation. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding the composition in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

To prepare the pharmaceutical composition, the Arid5a inhibitors or a salt thereof, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

For parenteral use, the carrier will usually comprise sterile water, though other ingredients, for example, for purposes such as aiding solubility or for preservation, may be included. Injectable suspensions may also be prepared, in which case appropriate liquid carriers, suspending agents, and the like may be employed. Accordingly, the pharmaceutically acceptable carrier can include alcohol, dimethyl sulfoxide (DMSO), physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The Arid5a inhibitors of the present disclosure also can be administered in the form of liposomes. Liposomes generally are derived from phospholipids or other lipid substances and are formed by mono- or multi-lamellar hydrated liquid crystals dispersed in an aqueous medium. Any nontoxic, physiologically acceptable and metabolizable lipid capable of forming liposomes can be used. The present compositions in liposome form can include, in addition to a compound of the present disclosure, stabilizers, preservatives, excipients, and the like. The preferred lipids are the phospholipids and the phosphatidyl cholines (lecithins), both natural and synthetic.

Pharmaceutical compositions for parenteral injection can include pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

The present compositions can include adjuvants such as preservatives, wetting agents, emulsifying agents, and dispersing agents. Prevention of the action of microorganisms can be ensured by the inclusion of various anti-bacterial and anti-fungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, monthly, or life-long administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the Arid5a inhibitor or an amount effective to treat an autoimmune disease or cancer, may be determined initially from the Examples described herein and adjusted for a specific desired Arid5a inhibitor using routine methods. In an embodiment, a therapeutically effective amount is an amount sufficient to achieve the desired therapeutic effects, e.g., a concentration of Arid5a inhibitor in plasma that ranges from about 1 nM to about 25 uM.

In an embodiment, the present subject matter includes a method of identifying candidate Arid5a inhibitors. An in silico analysis may be conducted to screen for candidate inhibitors. For example, molecular docking simulations can be used for screening a candidate inhibitor useful for treating autoimmune diseases and cancer. Candidate Arid5a inhibitors may be selected based on predicted interactions with a target domain in Arid5a. The target domain may be Pocket X, a feature of the Arid5a protein including, but not limited to, amino acids Glu53, Phe56, Leu57, Val58, Leu84, Tyr88, Leu133, Val134, Tyr137, Val138, His140, and Leu141. Candidate Arid5a inhibitors are then tested in vitro by examining the candidate inhibitors' effects on the stabilizing function of Arid5a on target mRNAs encoding pro-inflammatory mediators using a luciferase assay. The mRNAs can be of OX40, Il6, and Stat3. Candidate Arid5a inhibitors are then tested in vitro by examining the candidate inhibitors' effects on Arid5a binding activities to stem loops in the 3'UTR of target mRNAs and production of pro-inflammatory mediators using a RNA-protein binding system, PCR, and ELISA tests. Finally, the therapeutic potential of candidate Arid5a inhibitors may be assessed in vivo using commonly used representative experimental autoimmune models including MS, RA and psoriasis. A therapeutic potential can be determined according to clinical scores, cytokine levels, changes in $CD4^+$ T cell population, and OX40 expression.

The following examples illustrate the present teachings.

Example 1

Experimental Conditions

Experiments described herein were conducted using the following general experimental conditions.

Female C57BL/6 mice (6-8 weeks) were purchased originally from Charles River and maintained under specific pathogen-free conditions. All in vivo and in vitro animal experiments were performed using these mice at Laboratory of Physiology and Immunology, King Faisal University, Saudi Arabia, in accordance with institutional guidelines.

The peritoneal macrophages were stimulated in vitro with 0.5 μg/mL lipopolysaccharides (LPS) (Sigma-Aldrich) for 24 h. The $CD4^+$ $CD62L^+$ T cells were isolated and purified from spleen using the MACS isolation kit (Miltenyi). The T cells were cultured in the presence of anti-CD3/CD28 dynabeads (Invitrogen), recombinant mouse IL-6 (30 ng/mL; R&D Systems), recombinant transforming growth factor-β (TGF-β) (4 ng/mL; R&D Systems), anti-interferon-γ (IFN-γ) and anti-IL-4 (10 μg/mL; Biolegend) for 72 h to generate Th17 cells.

The mRNAs and cytokines were quantified as follows. A first strand of cDNA was synthesized from total RNA by using the TaqMan reverse transcription kit. The cDNA was amplified in the real-time PCR system ViiA7 using TaqMan gene expression assays of OX40 (Mm01261022_m1), Stat3 (Mm01219775_m1) and the endogenous control Gapdh (Mm99999915_g1). Kits, probes and reagents were from Applied Biosystems. The relative expression of mRNAs was calculated by ΔΔCt method. For cytokines quantification in serum and cell culture supernatants, ELISA kits of IL-17a, IL-6, TNF-α (Invitrogen) were used following the manufacturer's instructions.

Flow cytometry analysis was conducted using $CD4^+$ T cells cultured under Th17 cell-inducing conditions or $CD4^+$ T cells derived from CNS, which were fixed and stained with Per-CP-Cy5.5-conjugated anti-CD4 antibodies and PE-conjugated anti-OX40 antibodies (Biolegend). Analysis was carried out using Flowsight (Amnis).

Data are presented as mean±SD from representative experiment studied in triplicates out of at least three independent experiments produced similar results. The statistical significance between means was tested by one-way ANOVA. Two-way ANOVA was used to analyze the statistical significance of the data obtained from EAE, RA, and psoriasis models' clinical scores (*=$p<0.05$).

Example 2

Luciferase Assay of POE Inhibitory Effects on Arid5a Functions

The potential interaction between Arid5a inhibitor POE and Arid5a was predicted by in silico modeling. The effect of the potential interaction on the stabilizing function of Arid5a on the 3'UTR of target mRNAs was tested using a luciferase assay.

Figure 1B:
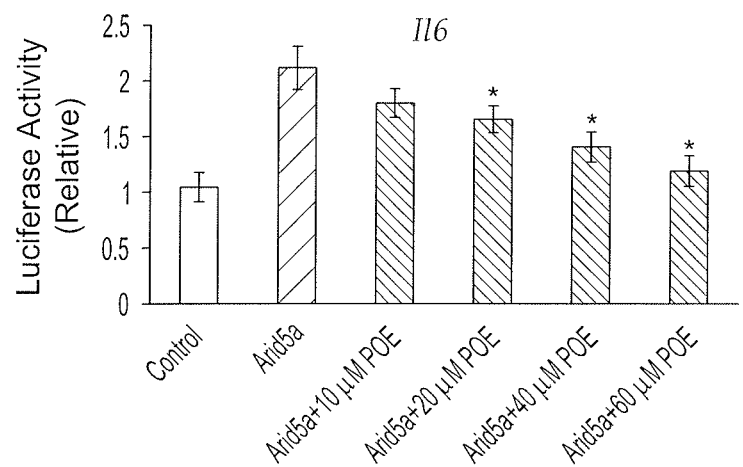
FIG. 1B depicts a graph of the effects of POE on Arid5a-mediated stability of the Il6 3'UTR.
Figure 1C:
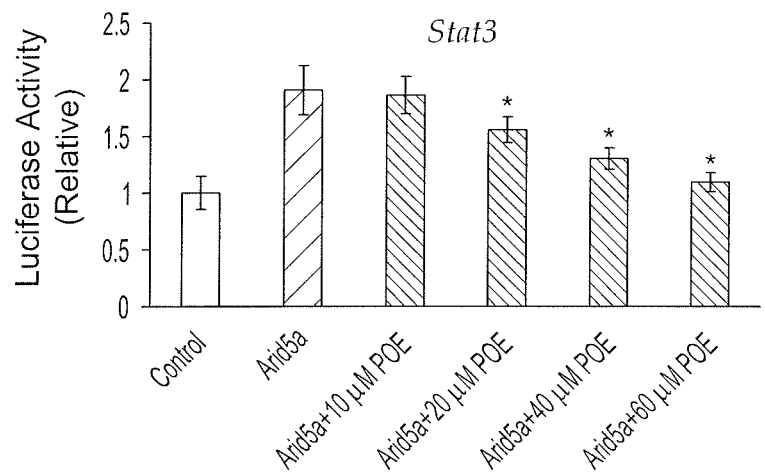
FIG. 1C depicts a graph of the effects of POE on Arid5a-mediated stability of the Stat3 3'UTR.

Briefly, HEK293T cells were transfected with luciferase pGL-3 and empty pcDNA3.1 plasmids (Control), or pGL-3 plasmid encoding the 3'UTR of OX40, Il6 or Stat3, together with Arid5a-expressing pcDNA3.1 plasmid. The cells were treated with DMSO (Control and Arid5a) or POE (10-60 μM) dissolved in DMSO. The mouse Arid5a (NP_001165676.1) cDNA (WT; ENSMUST00000115032.7) was cloned in a Flag-tagged pcDNA3.1 plasmid at Xba1 and Ecor1. Renilla-expressing plasmid was used as a control. Luciferase activity from cell lysates is shown relative to Control in FIGS. 1A-1C. The graphs depicted in FIGS. 1A-1C demonstrate that the Arid5a inhibitor POE inhibits Arid5a stabilizing function on the 3'UTR of OX40, Il6, and Stat3 mRNAs in a dose-dependent manner.

Example 3

Luciferase Assay of POE Inhibitory Effects on Pocket X-Mutant Arid5a

The Arid5a inhibitor POE was further predicted by in silico modeling to interact with Arid5a, specifically through Pocket X, a feature of the Arid5a protein including but not limited to amino acids Glu53, Phe56, Leu57, Val58, Leu84, Tyr88, Leu133, Val134, Tyr137, Val138, His140, and Leu141. The primary sequence of Arid5a (NP_001165676.1) was acquired from Ensemble and the 590 amino acid variant ENSMUST00000115032.7 was selected. The 3D coordinate of Arid5a was built to include residues 50-149 (SEQ ID NO: 1) of Arid5a. The binding sites of the target protein were identified using Q-site Finder and Pocket finder, and the binding domain (Pocket X) was chosen based on highest druggability score. Molecular docking simulation was carried out using SYBYLX 2.1 software (Tripos Associates Inc.) and Autodock 1.5.4 and 4.2 (Scripps Research). The candidate inhibitors were sorted based on predicted binding energy or CHEMPLP score.

The effect of the interaction between POE with specific residues in Pocket X on the stabilizing function of Arid5a on the 3'UTR of target mRNAs was confirmed by using a luciferase assay.

Briefly, HEK293T cells were transfected with luciferase pGL-3 and empty pcDNA3.1 plasmids (Control), or pGL-3 plasmid encoding the 3'UTR of OX40, Il6 or Stat3, together with Arid5a-expressing pcDNA3.1 plasmid. Substitution mutations were introduced to the wild-type (WT) Arid5a at Phe56, Leu84, Val134 and Tyr137. Single point mutations were used to substitute Phe56 (TTC) with Cys (TGC) and Val134 (GTC) with Ala (GCC). Sequential point mutations were used to substitute Leu84 (CTG) with Ala (GCG) and Tyr137 (TAT) with Ala (GCT). Luciferase activity from cell lysates is shown relative to Control in FIGS. 2A-2C.

Figure 2A:
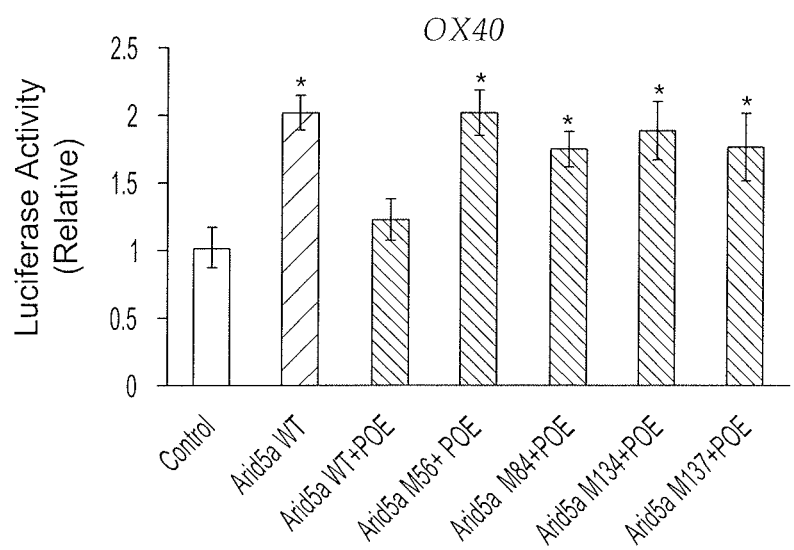
FIG. 2A depicts a graph of the effect of substitution mutations in Arid5a on POE-mediated inhibition of Arid5a stabilizing function on the OX40 3'UTR.
Figure 2B:
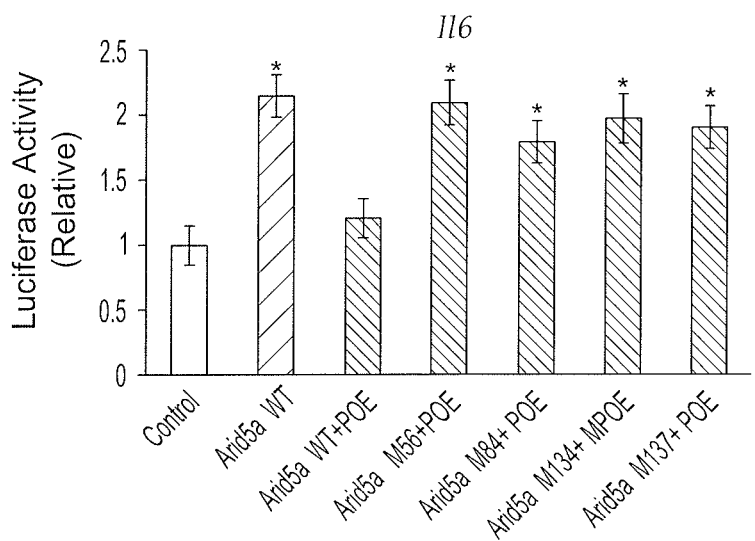
FIG. 2B depicts a graph of the effect of substitution mutations in Arid5a on POE-mediated inhibition of Arid5a stabilizing function on the Il6 3'UTR.
Figure 2C:
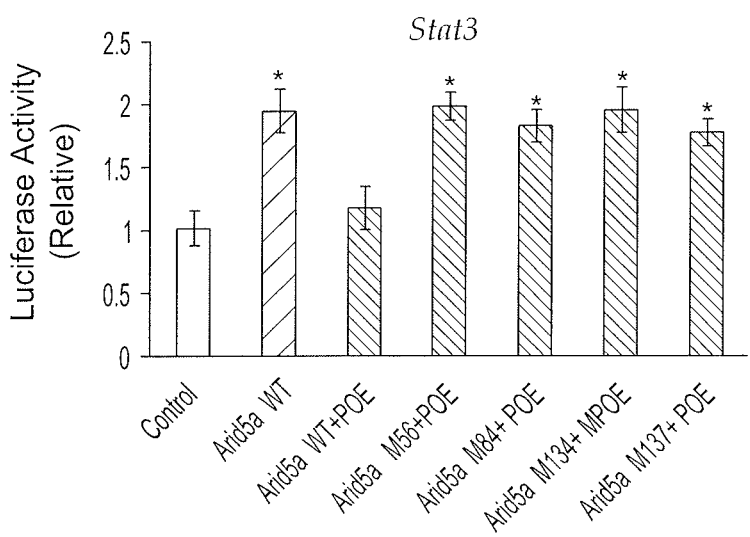
FIG. 2C depicts a graph of the effect of substitution mutations in Arid5a on POE-mediated inhibition of Arid5a stabilizing function on the Stat3 3'UTR.

As shown in FIG. 2A, substitution mutations at Phe56, Leu84, Val134 and Tyr137 of Pocket X abolish the inhibitory effects of POE (40 μM) on the stabilizing function of Arid5a on OX40 3'UTR. As shown in FIG. 2B, substitution mutations at Phe56, Leu84, Val134 and Tyr137 of Pocket X abolish the inhibitory effects of POE (40 µM) on the stabilizing function of Arid5a on Il6 3'UTR. As shown in FIG. 2C, substitution mutations at Phe56, Leu84, Val134 and Tyr137 of Pocket X abolish the inhibitory effects of POE (40 µM) on the stabilizing function of Arid5a on Stat3 3'UTR.

Example 4

Anti-Inflammatory Activity of POE

The anti-inflammatory activity of the Arid5a inhibitor POE was tested in vitro by measuring secretion of pro-inflammatory cytokines by macrophages and differentiated Th17 cells. Briefly, peritoneal macrophages were stimulated with LPS (0.5 µg/mL) for 24 h in presence or absence of POE (40 µM). Naïve (CD4$^+$CD62L$^+$) T cells from the spleen were differentiated under Th17-polarizing conditions for 72 h in presence or absence of POE (40 µM). Levels of IL-6 and TNF-α were quantified in supernatant of macrophage culture; the results are shown in FIGS. 3A and 3B. IL-17 was quantified in supernatant of polarized Th17 cell culture; the results are shown in FIG. 3C. The percentage of CD4$^+$ OX40$^+$ T cells in the polarized Th17 cells was determined using flow cytometry; the results are shown in FIG. 3D. Stat3 mRNA expression in the polarized Th17 cells was quantified by real-time PCR and normalized to Gapdh mRNA; the results are shown relative to those of untreated Th17 cells in FIG. 3E.

As shown in FIG. 3A, POE reduces the level of IL-6 in cell culture supernatant of LPS-stimulated macrophages compared to LPS alone. As shown in FIG. 3B, POE does not affect the level of TNF-α in cell culture supernatant of LPS-stimulated macrophages compared to LPS alone. As shown in FIG. 3C, POE reduces the level of IL-17 in cell culture supernatant of polarized Th17 cells compared to untreated Th17 cells. As shown in FIG. 3D, POE reduces the frequency of CD4$^+$OX40$^+$ T cells in polarized Th17 cells compared to untreated Th17 cells. As shown in FIG. 3E, POE reduces the expression of Stat3 mRNA in polarized Th17 cells compared to untreated Th17 cells.

Example 5

RNA-Arid5a Binding Assay

Figure 4:
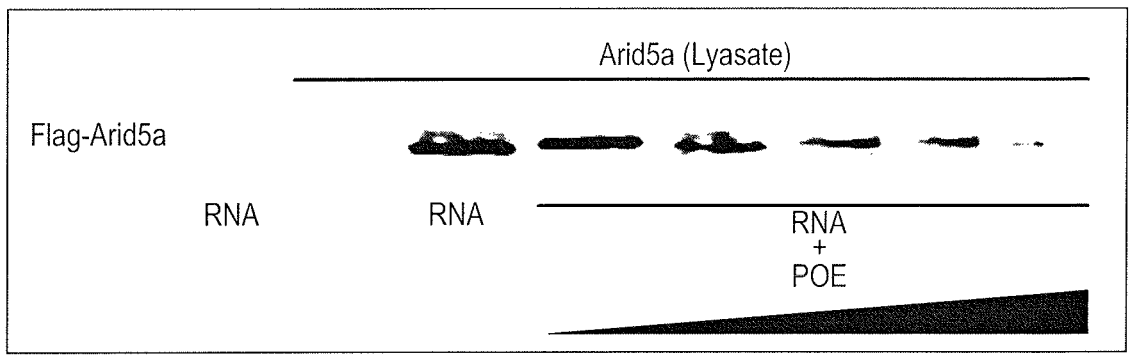
FIG. 4 depicts the effect of POE on Arid5a binding to the alternative decay element (ADE)-like stem loop in the OX40 3'UTR.

An RNA-protein binding assay was performed to confirm that POE inhibits the physical binding of Arid5a to the (ADE)-like stem loop in the OX40 3'UTR. Briefly, a 3'-biotinylated OX40 ADE-like stem loop (RNA; 5'-UC-CACACCGUUCUAGGUGCUGG-3') (SEQ ID NO: 2) was conjugated to streptavidin beads. The OX40 ADE-like stem loop/streptavidin bead conjugate was then mixed with Flag-Arid5a-enriched HEK293T cell lysate, washed, and proteins bound to RNA were eluted for immunoblot. Anti-Flag antibodies were used to detect Flag-Arid5a in the eluate by SDS-PAGE analysis. As shown in FIG. 4, POE inhibited the physical binding of Arid5a to OX40 ADE-like stem loop in a concentration-dependent manner.

Example 6

Therapeutic Effects of POE in Experimental Multiple Sclerosis

Briefly, EAE was induced in C57BL/6 female mice using MOG$_{35-55}$ (200 µg) emulsified in complete Freund's adjuvant containing 10 mg/mL heat-killed *Mycobacterium tuberculosis* H37Ra. Mice received two intraperitoneal injections of pertussis toxin (500 ng) on days 0 and 2. The mice received one intraperitoneal injection of POE (0.5 mg) or corn oil per day starting from day 0 for four consecutive days. Serum levels of IL-6 and TNF-α were quantified on day 24. Encephalitogenic CD4$^+$ T cells were isolated from lymph nodes of EAE mice and re-stimulated with MOG$_{35-55}$ (30 µg/mL) and IL-23 (23 ng/mL) for 72 h; thereafter IL-7 was quantified in cell culture supernatant by ELISA. OX40 mRNA and protein were quantified in CD4$^+$ T cells isolated from the CNS of EAE mice 10 days after disease induction. The mRNA was quantified by real-time PCR, normalized to Gapdh mRNA and presented relative to that of corn oil-treated EAE mice. The percentage of CD4$^+$/OX40$^+$ T cells was analyzed using flow cytometry.

Figure 5A:
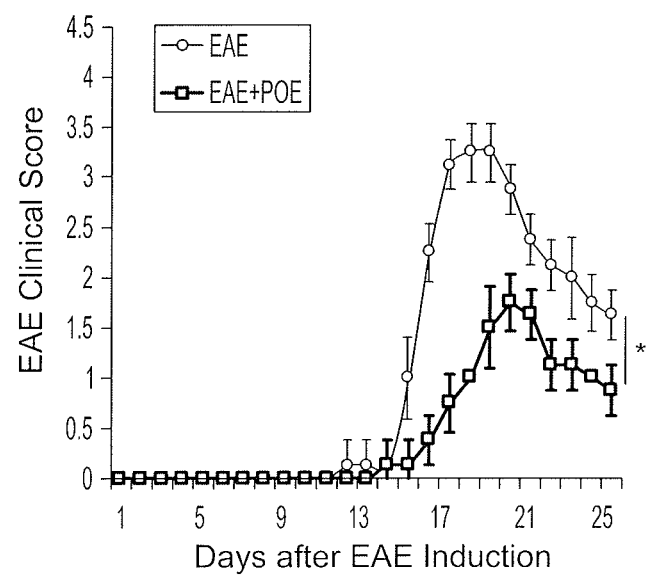
FIG. 5A depicts a graph of EAE score over time with and without POE treatment.
Figure 5B:
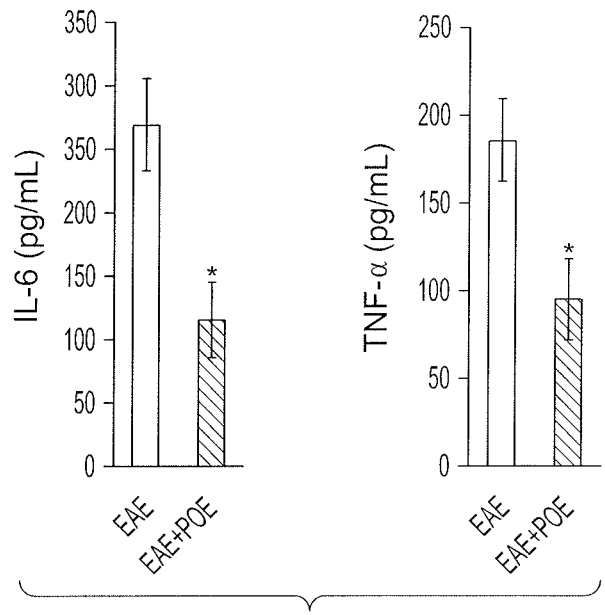
FIG. 5B depicts a graph of IL-6 and TNF-α serum levels in the EAE model with and without treatment with POE.
Figure 5C:
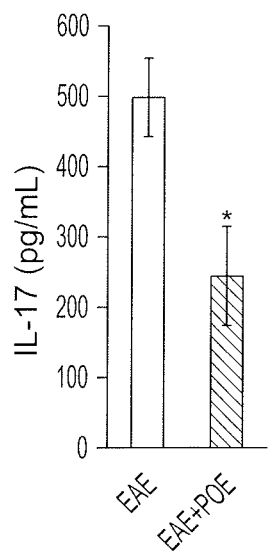
FIG. 5C depicts a graph of IL-17 production by encephalitogenic CD4$^+$ T cells in response to restimulation in the EAE model with and without treatment with POE.

As shown in FIG. 5A, POE treatment reduces EAE clinical scores compared to corn oil-treated mice (EAE). As shown in FIG. 5B, POE reduces serum levels of IL-6 and TNF-α compared to corn oil-treated mice (EAE). As shown in FIG. 5C, POE reduces the level of IL-17 in culture supernatant of encephalitogenic CD4$^+$ T cells in response to restimulation compared to corn oil-treated mice (EAE). As shown in FIG. 5D, POE reduces the expression of OX40 mRNA in CD4$^+$ T cells isolated from the CNS of EAE mice. As shown in FIG. 5E, POE reduces the frequency of CD4$^+$OX40$^+$ T cells in the CNS of EAE mice.

Example 7

POE Analogs

Further molecular docking simulations were performed to look for potential binding between Arid5a and several POE analogs, and then define common characteristics for such analogs. These simulations identified a common structure of the POE analogs that would interact with Arid5a, comprising substituted oxa/thiadiazole and triazole compounds of the formula:

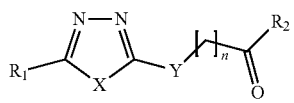

wherein each of $R_1$ and $R_2$ is independently selected from H, alkyl, phenyl, substituted phenyl, a 5-membered heteroaryl, and 6-membered heteroaryl; each of X and Y is independently selected from S, O, and NH; and n is an integer selected from 0, 1, and 2. Arid5a inhibitors identified in silico include but are not limited to POE analogs POE A1 (2-[5-methyl-1,3,4-oxadiazol-2-yl)sulfanyl]-1-phenylethan-1-one), POE A2 (2-[(5-methyl-1,3,4-thiadiazol-2-yl) amino]-1-phenylethan-1-one), POE A3 (2-Propanone, 1-[[5-(3-pyridinyl)-1,3,4-oxadiazol-2-yl]thio]-). The compounds POE A1-A3 were selected as representative illustrative examples for further studies. The potential binding between POE analogs A1-A3 and Arid5a was predicted to be relatively strong, including a number of hydrogen bonds and pi interactions with respective binding energies of −6.16, −6.18 and, −6.76, and −6.03, respectively.

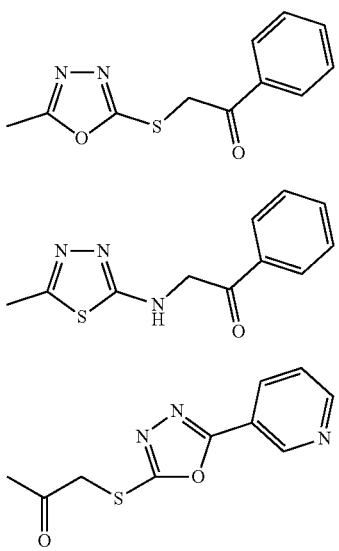

Example 8

Luciferase Assay of POE Analogs Inhibitory Effects on Arid5a Functions

HEK293 T cells (ATCC) were transfected (Lipofectamine LTX; Invitrogen) with luciferase pGL-3 and empty peDNA 3.1 plasmids (Control), or pGL-3 plasmid encoding the 3'UTR of IL6 together with Arid5a-expressing pcDNA3.1 plasmid. Renila-expressing plasmid was used as a Control. The cells were treated with DMSO (Control and Arid5a) or POE or its analogs A1-3 (40 µM; Aurora) dissolved in DMSO. The mouse Arid5a (NP_001165676.1) cDNA (WT; ENSMUST00000115032.7) was cloned in a Flag-tagged pcDNA3.1 plasmid at Xba1 and EcoR1.

To examine whether the Arid5a inhibitors interact with the target domain of Arid5a (Pocket X), substitution mutations were introduced to the wild-type (WT) Arid5a at Phe56, Tyr137 and His140 to produce mutant Arid5a (mArid5a). Mutations were introduced to substitute Phe56 with Cys, Tyr137 with Ala, and His140 with Ala. Luciferase activity from cell lysates was quantified using a Dual Luciferase kit (Promega) and the results were shown relative to the Control.

Figure 6:
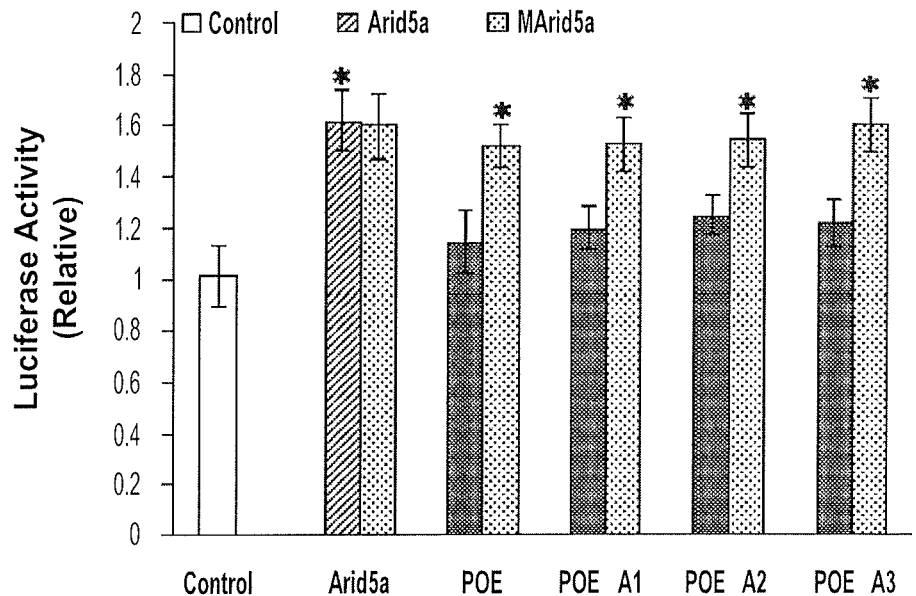

As shown in FIG. 6, POE and its analogs A1-3 (40 µM) abolished the stabilizing function of Arid5a and shortened the half-life of Il6 3'UTR. These results confirm that the representative POE analogs POE A1-A3 are efficient Arid5a inhibitors. Further investigations showed that substitution mutations at Phe56, Tyr137, and His140 of the target domain of Arid5a abolish the inhibitor effects of the Arid5a inhibitors and reinstated Arid5a function (See FIG. 6). These results confirm that the interaction between the Arid5a inhibitors and the target domain of Arid5a (Pocket X) is required for the Arid5a inhibitors to inhibit Arid5a's stabilizing function.

Example 9

Therapeutic Effects of POE and POE Analogs in Experimental Rheumatoid Arthritis

Collagen-induced arthritis (CIA) was induced following a modified method described previously (Nakahama et al 2011). Briefly, chicken type II collagen (CII; Sigma Aldrich) was dissolved in 10 mM acetic acid (4 mg/ml) at 4° C. overnight. C57BL mice (n=5) were injected at the base of the tail with 100 µg CII emulsified in complete Freund adjuvant (CFA, H37Ra; Difco Laboratories). The same injection was repeated 14 days later. Evaluation of CIA was as follows: 0=normal, 1=edema or swelling, 2=edema and erythema at foot or ankle, 3=edema and erythema from ankle to the tarsal bone, 4=edema at entire leg and joint distortion. On days 0, 3, 6, 9, 12, 15, and 18 after first immunization, the mice received one interperitoneal injection of corn oil (vehicle) or POE, POE A1, or POE A2 (0.25 mg). Serum levels of IL-6 were quantified on day 45 after first immunization using ELISA (Invitrogen), following manufacturer's instructions.

Flow cytometry analysis was conducted on CD4$^+$ T cells isolated from secondary lymphoid organs on day 45 after first immunization using a MACS isolation kit (Miltenyi). The cells were stimulated with 50 ng/ml phorbol 12-myristate 13-acetate (Sigma-Aldrich) and 800 ng/ml ionomycin (Sigma-Aldrich) for 4 hours, and Protein Transport Inhibitor (Invitrogen) was added for the last two hours. PerCP-Cy5.5-conjugated anti-CD4 antibodies (eBioscience) were used for surface staining. An Intracellular Staining Kit (Life Technologies) and PE-conjugated anti-IL-17 antibodies (eBioscience) were used. Analysis was carried out using a FlowSight system (Amnis).

Figure 7A:
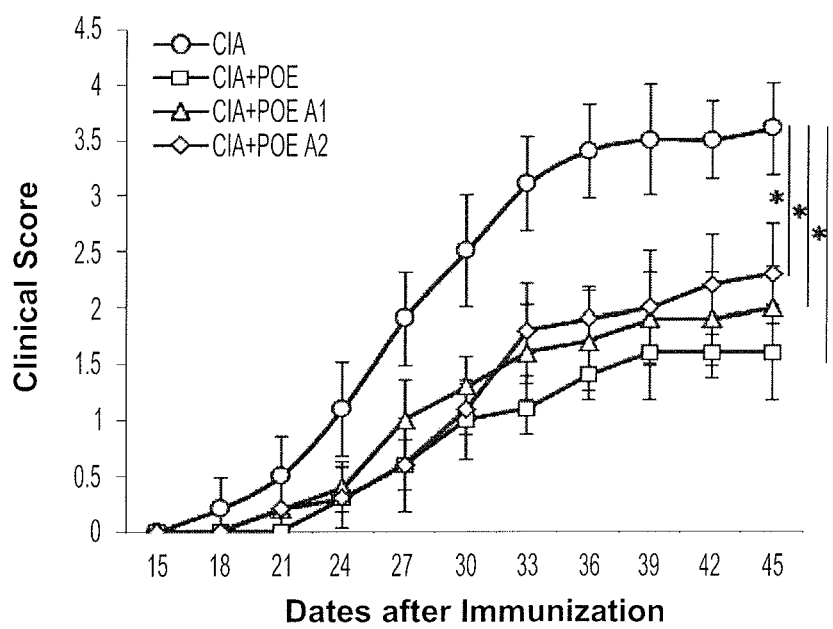
FIG. 7A depicts a graph of CIA clinical score over time with and without treatment with POE or its example analogs POE A1 or POE A2.
Figure 7B:
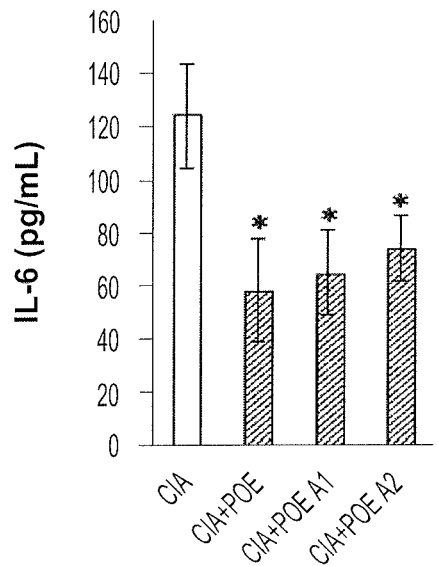
FIG. 7B depicts a graph of IL-6 serum level in the CIA model with and without treatment with POE or its example analogs POE A1 or POE A2.
Figure 7C:
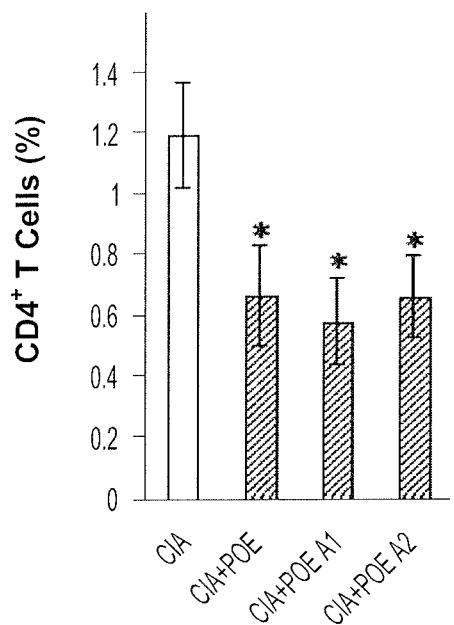
FIG. 7C depicts a graph of the percentage of CD4$^+$IL-17$^+$ T cells in secondary lymphoid organs in the CIA model with and without treatment using POE or its example analogs POE A1 or POE A2.

As shown in FIG. 7A, parenteral treatment with POE or its example analogs POE A1 and POE A2 comparably reduced CIA clinical scores compared to corn oil-treated mice (CIA). As depicted in FIG. 7B, POE or its analogs POE A1 and POE A2 reduced serum levels of IL-6 compared to CIA mice. Furthermore, POE or its analogs POE A1 and POE A2 reduced the frequency of CD4$^+$IL-17$^+$ cells in the secondary lymphoid organs compared to CIA mice (FIG. 7C).

Example 10

Therapeutic Effects of POE and POE Analogs in Experimental Psoriasis

Experimental psoriasis was induced following a modified method described previously (Sun et al. 2013). To induce disease in male BALB/c mice (6-8 weeks; n=6), imiquimod (IMG; Sichuan Med-Shine Pharmaceutical) at 5% was applied topically at 20 mg/cm$^2$ on the inside of the right ear for 8 consecutive days. An evaluation system for assessment of erythema and thickness of the ear was developed. Erythema was assessed using a table with red taints (0-4) and ear thickness (0-4) measured using a digital caliber on days 2, 4, 6, and 8 after first IMQ application. The sum of the two parameters scores (ranging from 0-8) was used to indicate the overall clinical score.

Treatment ointment was prepared by mixing 1 mg of DMSO-dissolved POE or its representative analogs including POE A2 or POE A3 with 20 gm of Vaseline Petroleum Jelly Original (vehicle, Unilever Inc.); the mixture was then incubated at room temperature overnight. From day 0 to day 8 the mice were treated topically with the treatment ointment (40 mg/cm$^2$) or Vaseline (IMQ/control).

The mRNAs encoding Il6 and Il17a were isolated from whole biopsies of the ear (day 8) and reverse transcribed to make cDNA. The cDNA was then amplified by real-time PCR using TaqMan Gene Expression Assays (Mm00446190_ml, Mm00439618_ml, respectively;

Applied Biosystems). The relative expression of mRNAs was calculated by the ΔΔCt method and presented relative to that of IMQ control mice.

Figure 8A:
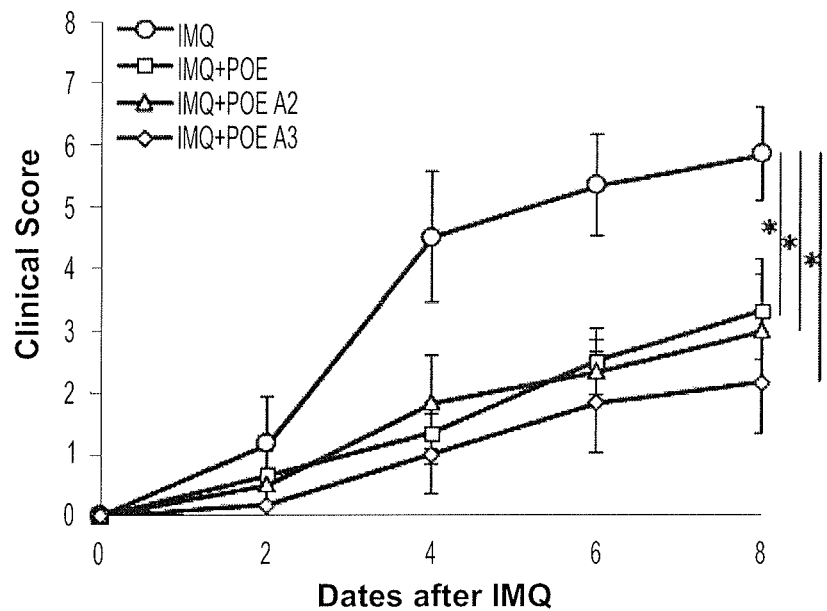
FIG. 8A depicts a graph of the score of IMQ-induced-psoriasis model over time with and without treatment with POE or its example analogs POE A2 or POE A3.
Figure 8B:
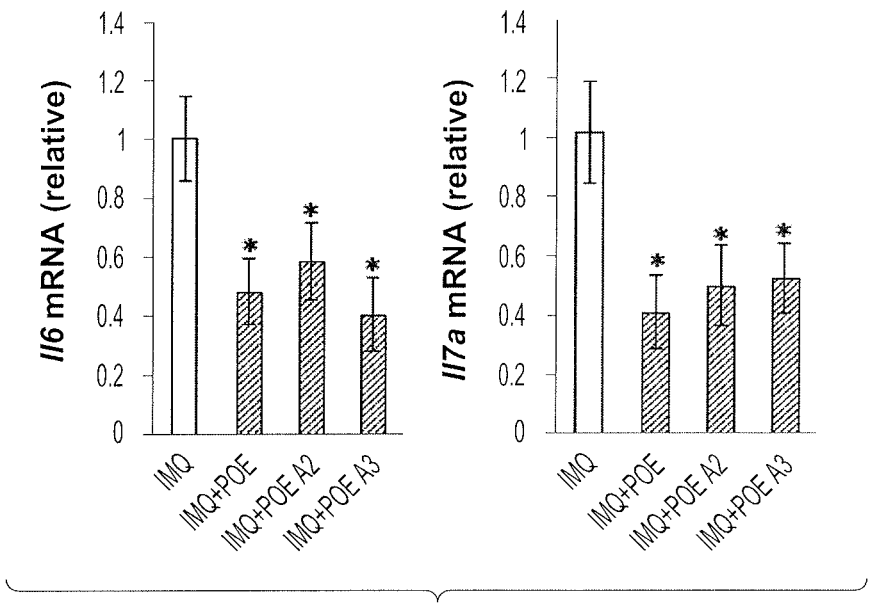
FIG. 8B depicts a graph of mRNA expression of Il6 and Il17a in a biopsy from IMQ-induced-psoriasis model with and without treatment with POE or its example analogs POE A2 or POE A3.

As depicted in FIG. 8A, topical treatment with POE or its example analogs POE A2 and POE A3 comparably reduced clinical scores (erythema and thickness of the right ear) of IMQ-induced psoriasis compared to Vaseline-treated mice (IMQ). Furthermore, POE or its analogs POE A2 and POE A3 suppressed mRNA expression of the pro-inflammatory cytokines Il6 and Il17a in the whole biopsies of the right ear (FIG. 8B).

Example 11

Cancer

Breast cancer cells of the cell line MDA-MB-231, prostate cancer cells of the cell line LNCaP, and lung cancer cells of the cell line A549 were obtained from ATCC. The cells were cultured in DMEM/F-12 medium containing 10% FBS and antibiotic antimycotic solution (Sigma-Aldrich). Cell Counting Kits (CCK-8; Dojindo) were used to perform proliferation assays. Briefly, cells of the various cell lines were seeded in 96-well plates for 48 hours with tetrazolium added for the last 4 hours. Color formation was quantified using a plate reader, and proliferation results in the presence of DMSO-dissolved POE or its example analogs POE A1-A3 were presented relative to DMSO-treated cells (control). All data are presented as cell viability (%).

Figure 9A:
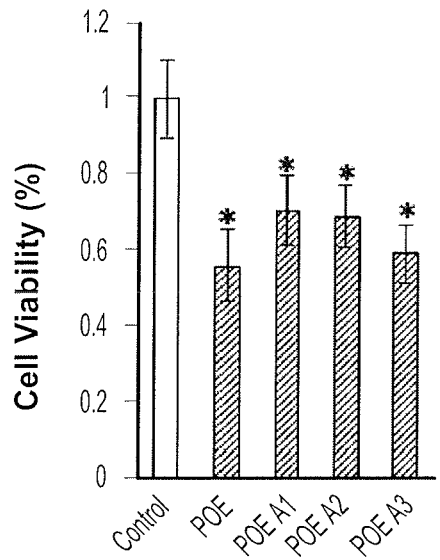
FIG. 9A depicts a graph of the anti-proliferative effects of POE and its example analogs POE A1-A3 on MDA-MB-231 breast cancer cells.
Figure 9B:
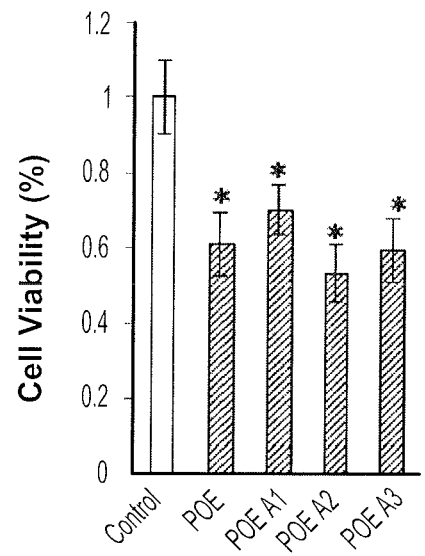
FIG. 9B depicts a graph of the anti-proliferative effects of POE and its example analogs POE A1-A3 on LNCaP prostate cancer cells.
Figure 9C:
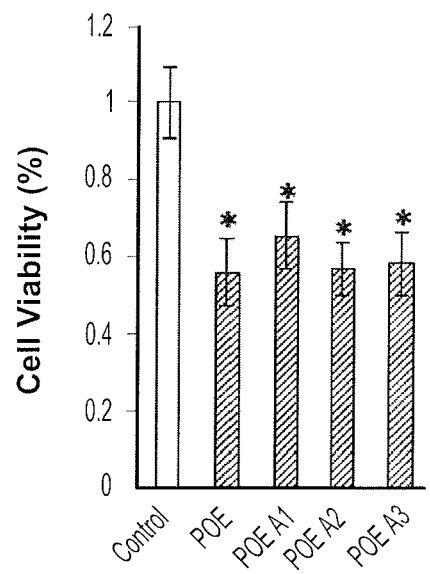
FIG. 9C depicts a graph of the anti-proliferative effects of POE and its example analogs POE A1-A3 on A549 lung cancer cells.

Viability studies using MDA-MB-231, LNCaP, and A549 cells showed that the average half maximal inhibitory concentrations ($IC_{50}$) of POE and its analogues POE A1-3 were 27.8 μM (MD-MB-231), 34.6 μM (LNCaP), and 28.4 μM (A549). The anti-proliferative effects of POE and its example analogs POE A1-A3 on cancer cell lines are shown in FIGS. 9A-9C. As shown in FIG. 9A, POE and its analogs POE A1-A3 (20 μM) suppressed viability of MDA-MB-231 cells with an average of 64%. As shown in FIG. 9B, POE and its analogs POE A1-A3 (25 μM) suppressed proliferation of LNCaP cells with an average of 61%. As shown in FIG. 9C, POE and its analogs POE A1-A3 (20 μM) suppressed proliferation of A549 cells with an average of 59%.

It is to be understood that the therapeutic agents for treating and preventing autoimmune diseases and cancer and a screening method is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating an autoimmune disease, comprising administering to a subject in need thereof an effective amount of one or more Arid5a inhibitors comprising a compound having a chemical structure according to the general formula:

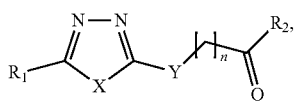

wherein each of $R_1$ and $R_2$ is independently selected from the group consisting of H, alkyl, phenyl, substituted phenyl, a 5-membered heteroaryl, and a 6-membered heteroaryl; X is selected from the group consisting of S and O; Y is selected from the group consisting of S and NH; and n is an integer selected from 0, 1, and 2; and wherein the autoimmune disease is selected from the group consisting of multiple sclerosis, rheumatoid arthritis, and psoriasis.

2. The method of claim 1, wherein the Arid5a inhibitor comprises a compound selected from the group consisting of:

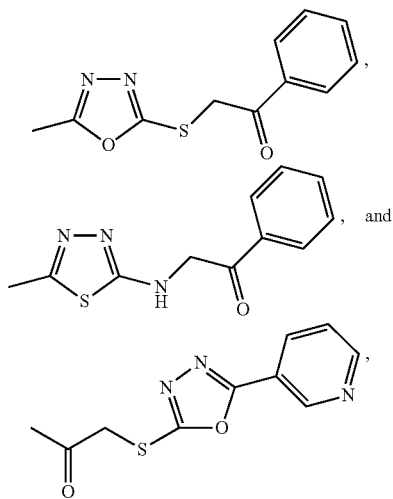

or a pharmaceutically acceptable salt thereof.

3. A method of treating cancer, comprising administering to a subject in need thereof an effective amount of one or more Arid5a inhibitors comprising a compound having a chemical structure according to the general formula:

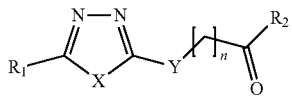

wherein each of $R_1$ and $R_2$ is independently selected from the group consisting of H, alkyl, phenyl, substituted phenyl, a 5-membered heteroaryl, and a 6-membered heteroaryl; X is selected from the group consisting of S and O; Y is selected from the group consisting of S and NH; and n is an integer selected from 0, 1, and 2; and wherein the cancer is selected from the group consisting of breast cancer, prostate cancer, or lung cancer.

4. The method of claim 3, wherein the Arid5a inhibitor comprises a compound selected from the group consisting of:

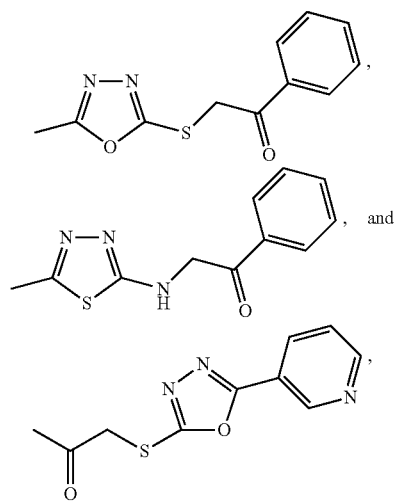

or a pharmaceutically acceptable salt thereof.

* * * * *